(12) United States Patent
Westfall et al.

(10) Patent No.: US 11,642,486 B2
(45) Date of Patent: May 9, 2023

(54) PORTABLE OXYGEN CONCENTRATOR RETROFIT SYSTEM AND METHOD

(71) Applicant: Breathe Technologies, Inc., Irvine, CA (US)

(72) Inventors: Tom Westfall, Irvine, CA (US); Enrico Brambilla, Irvine, CA (US)

(73) Assignee: BREATHE TECHNOLOGIES, INC., Irvine, CA (US)

( * ) Notice: Subject to any disclaimer, the term of this patent is extended or adjusted under 35 U.S.C. 154(b) by 392 days.

(21) Appl. No.: 16/862,240

(22) Filed: Apr. 29, 2020

(65) Prior Publication Data

US 2020/0360644 A1    Nov. 19, 2020

Related U.S. Application Data

(60) Provisional application No. 62/849,705, filed on May 17, 2019.

(51) Int. Cl.
*A61M 16/00* (2006.01)
*A61M 16/10* (2006.01)

(52) U.S. Cl.
CPC ...... *A61M 16/101* (2014.02); *A61M 16/0003* (2014.02); *A61M 16/009* (2013.01); *A61M 16/0063* (2014.02); *A61M 16/105* (2013.01); *A61M 2016/0027* (2013.01); *A61M 2202/0208* (2013.01); *A61M 2205/3355* (2013.01)

(58) Field of Classification Search
CPC ............ A61M 16/101; A61M 16/0003; A61M 16/0063; A61M 2016/0027; A61M 2202/0208; A61M 2205/3355; B01D 53/053
See application file for complete search history.

(56) References Cited

U.S. PATENT DOCUMENTS

| | | |
|---|---|---|
| 6,605,136 B1 | 8/2003 | Graham et al. |
| 6,824,590 B2 | 11/2004 | Dee et al. |
| 7,066,985 B2 | 6/2006 | Deane et al. |
| 7,135,059 B2 | 11/2006 | Deane et al. |
| 7,279,029 B2 | 10/2007 | Occhialini et al. |
| 7,438,745 B2 | 10/2008 | Deane et al. |
| 7,473,299 B2 | 1/2009 | Occhialini et al. |
| 7,585,351 B2 | 9/2009 | Deane et al. |
| 7,686,870 B1 | 3/2010 | Deane et al. |
| 7,708,802 B1 | 5/2010 | Deane et al. |
| 7,730,887 B2 | 6/2010 | Deane et al. |
| 7,753,996 B1 | 7/2010 | Deane et al. |
| 7,780,768 B2 | 8/2010 | Taylor et al. |
| 7,841,343 B2 | 11/2010 | Deane et al. |
| 7,857,894 B2 | 12/2010 | Taylor et al. |
| 7,922,789 B1 | 4/2011 | Deane et al. |

(Continued)

OTHER PUBLICATIONS

US 10,265,491 B2, 04/2019, Allum et al. (withdrawn)
European Search Report for EP20173839; dated Sep. 29, 2020.

*Primary Examiner* — Philip R Wiest
*Assistant Examiner* — Sarah B Lederer
(74) *Attorney, Agent, or Firm* — Stetina Brunda Garred & Brucker

(57) ABSTRACT

A portable oxygen concentrator retrofit system and method in which an existing portable oxygen concentrator may be retrofitted to output an enriched oxygen gas at a flow rate suitable for use in a patient ventilation system without the need for an external source of compressed gas.

19 Claims, 3 Drawing Sheets

(56) References Cited

U.S. PATENT DOCUMENTS

| | | |
|---|---|---|
| 8,142,544 B2 | 3/2012 | Taylor et al. |
| 8,366,815 B2 | 2/2013 | Taylor et al. |
| 8,377,181 B2 | 2/2013 | Taylor et al. |
| 8,440,004 B2 | 5/2013 | Taylor et al. |
| 8,568,519 B2 | 10/2013 | Taylor et al. |
| 8,580,015 B2 | 11/2013 | Taylor et al. |
| 8,702,841 B2 | 4/2014 | Taylor et al. |
| 9,220,864 B2 | 12/2015 | Taylor et al. |
| 9,283,346 B2 | 3/2016 | Taylor et al. |
| 9,592,360 B2 | 3/2017 | Taylor et al. |
| 9,907,926 B2 * | 3/2018 | Allum ............... A61M 16/209 |
| 9,995,645 B2 | 6/2018 | Allum |
| 10,004,869 B2 | 6/2018 | Taylor et al. |
| 10,384,028 B2 | 4/2019 | Allum et al. |
| 10,792,453 B2 | 10/2020 | Allum |
| 10,946,161 B2 | 3/2021 | Oddo et al. |
| 11,071,841 B2 | 7/2021 | Edwards |
| 11,123,512 B2 | 9/2021 | Allum |
| 11,278,698 B2 | 3/2022 | Romano et al. |
| 11,491,293 B2 | 11/2022 | Hete et al. |
| 2002/0040714 A1 * | 4/2002 | Yagi .................. A61M 16/00 128/207.18 |
| 2005/0072423 A1 | 4/2005 | Deane et al. |
| 2005/0072426 A1 | 4/2005 | Deane et al. |
| 2006/0090759 A1 | 5/2006 | Howes et al. |
| 2006/0124128 A1 | 6/2006 | Deane et al. |
| 2006/0174878 A1 | 8/2006 | Jagger et al. |
| 2006/0292654 A1 | 12/2006 | Reardon |
| 2007/0039466 A1 * | 2/2007 | Nawata ................ B01D 53/053 95/96 |
| 2007/0125377 A1 * | 6/2007 | Heinonen ........... A61M 16/203 128/204.21 |
| 2008/0072907 A1 | 3/2008 | Deane et al. |
| 2008/0110338 A1 | 5/2008 | Taylor et al. |
| 2008/0202337 A1 | 8/2008 | Taylor et al. |
| 2009/0126736 A1 | 5/2009 | Taylor et al. |
| 2009/0131763 A1 | 5/2009 | Taylor et al. |
| 2014/0190348 A1 * | 7/2014 | Richey, II ......... B01D 53/0423 96/116 |
| 2017/0113013 A1 | 4/2017 | Allum |
| 2017/0143926 A1 | 5/2017 | Allum et al. |
| 2017/0340851 A1 | 11/2017 | Allum et al. |
| 2017/0348501 A1 | 12/2017 | Taylor et al. |
| 2017/0361052 A1 | 12/2017 | Taylor et al. |
| 2018/0001048 A1 * | 1/2018 | Allum ................ A61M 16/101 |
| 2018/0200474 A1 | 7/2018 | Allum et al. |
| 2018/0200475 A1 | 7/2018 | Allum et al. |
| 2018/0364119 A1 | 12/2018 | Allum |
| 2018/0369531 A1 | 12/2018 | Taylor et al. |
| 2019/0175860 A1 | 6/2019 | Allum et al. |
| 2020/0155783 A1 | 5/2020 | Allum et al. |

\* cited by examiner

PORTABLE OXYGEN CONCENTRATOR RETROFIT SYSTEM AND METHOD

CROSS-REFERENCE TO RELATED APPLICATIONS

This application relates to and claims the benefit of U.S. Provisional Application No. 62/849,705, filed May 17, 2019 and entitled "PORTABLE OXYGEN CONCENTRATOR RETROFIT SYSTEM AND METHOD," the entire contents of which is expressly incorporated herein by reference.

STATEMENT RE: FEDERALLY SPONSORED RESEARCH/DEVELOPMENT

Not Applicable

BACKGROUND

1. Technical Field

The present disclosure relates generally to portable oxygen concentrators and, more particularly, to a method of retrofitting a portable oxygen concentrator to interface with and enable use in a patient ventilation system.

2. Related Art

A wide range of clinical conditions may require some form of ventilation therapy, whereby the patient's work of breathing is assisted by the flow of pressurized gas from a ventilator to the patient's airway. These conditions may include hypoxemia, various forms of respiratory insufficiency, and airway disorders. There are also non-respiratory and non-airway diseases that require ventilation therapy, such as congestive heart failure and neuromuscular diseases.

To improve the quality of life of many patients who require long-term ventilation therapy, ventilation systems have been developed which are miniaturized and portable. Some of these systems, for example, the Life2000™ system by Breathe Technologies, Inc., are so lightweight and compact that in their extended range or stand-alone configurations, they are wearable by the patient. These systems require a source of pressurized ventilation gas to operate. In the stationary or extended range configuration, the source of pressurized gas may be a stationary compressor unit, which may be kept in a patient's home. In the stand-alone configuration, which may be generally used when the patient is outside the home, the portable, wearable ventilator generally may receive its ventilation gas from a pressurized gas cylinder or a portable compressor.

Many of the above clinical conditions and other clinical conditions may also require or benefit from supplemental oxygen therapy, whereby the gas introduced to the patient's airway is augmented by the presence of additional oxygen such that the patient inspires gas having oxygen levels above atmospheric concentration (20.9% at 0% humidity). Supplemental oxygen therapy requires the patient to receive supplemental oxygen gas from an oxygen gas source, which is typically a compressed or cryogenic oxygen cylinder or an oxygen gas generator. For many years, patients who wished to be mobile relied on oxygen cylinders. However, in recent years, miniaturization and improvements in battery technology have resulted in the development of portable oxygen concentrators (POCs).

Portable oxygen concentrators typically operate by pressure swing adsorption (PSA), in which ambient air is pressurized by a compressor and passed through an adsorbent sieve bed. The sieve bed is typically formed of a zeolite which preferentially adsorbs nitrogen when at high pressure while oxygen passes through. Once the sieve bed reaches its capacity to adsorb nitrogen, the pressure can be reduced. This reduction in pressure causes the adsorbed nitrogen to be desorbed so it can be purged, leaving a regenerated sieve bed that is again ready to adsorb nitrogen. With repeated cycles of this operation, an enriched oxygen gas may be generated. Typically, portable oxygen concentrators have at least two sieve beds so that one may operate while the other is being purged of the nitrogen and vented. Typical portable oxygen concentrators today output an enriched oxygen gas with a purity of around 87-96% oxygen. Among existing oxygen concentrators today which may be considered portable (especially by an individual suffering from a respiratory condition), there are generally two types available. The first type, which is larger and heavier, is usually capable of continuous flow delivery. Models of this type typically weigh between 4-7 kg, have maximum flow rates of around 2-3 liters per minute or less, and are generally configured with wheels and a handle, often mimicking the appearance of a suitcase. The second type are lighter units more suitable for being carried or worn in a satchel, handbag, or backpack. Models of this type typically weigh less than 2.5 kg and are usually limited to pulsed delivery modes with maximum flow rates of around 1 liter per minute or less.

Portable oxygen concentrators have a substantial cost and convenience advantage over pressurized oxygen cylinders, due to the pressurized oxygen cylinders requiring ongoing refilling or replacement. Additionally, portable oxygen concentrators are considered to be significantly safer than pressurized oxygen cylinders. This safety consideration can have a substantial impact on a patient's quality of life, because many portable oxygen concentrators have been approved by the FAA for use by travelers on commercial airlines, whereas oxygen cylinders are universally banned on commercial flights. Consequently, patients with pressurized oxygen cylinders must make expensive and time-consuming preparations with an airline ahead of time, or forego airline travel entirely.

For patients with conditions where assistance with the work of breathing is not required, supplemental oxygen therapy alone, without ventilation therapy, may be sufficient. However, for many patients, combined ventilation therapy and supplemental oxygen therapy may be a more optimal treatment. In healthy patients, sufficient ventilation to perform the work of breathing may typically require minute ventilation rates of between 5 and 8 L/min while stationary, which may double during light exercise, and which may exceed 30 L/min during heavy exercise. Patients suffering from respiratory conditions may require substantially higher rates, and substantially higher instantaneous rates. This is especially true when these patients are outside the home and require portability, as at these times such patients are often also involved in light exercise.

It may thus be seen that patients who would prefer to receive this combined mode of treatment are substantially limited, due to the fact that in many cases existing portable oxygen concentrators do not output gas at pressures and/or volumes high enough to be used with a wearable, portable ventilator without the presence of an additional source of compressed gas. As such, when maximum portability is desired, these patients must either forego the substantial benefits of a portable oxygen concentrator and return to oxygen cylinders (which may output oxygen gas at the higher pressures and flow rates required for ventilation therapy), or additionally have with them a portable compressor, with the portable oxygen concentrator, the portable compressor, and the wearable ventilator interfaced together. Existing systems and methods are generally deficient in maximizing patient mobility by providing a combined supplemental oxygen/ventilation system that is lightweight and small enough to be entirely carried and/or worn by the patient.

BRIEF SUMMARY

To solve these and other problems, a portable oxygen concentrator retrofit system and method is contemplated in which an existing portable oxygen concentrator may be retrofitted to output an enriched oxygen gas at a flow rate suitable for use in a patient ventilation system without the need for an external source of compressed gas.

A method of retrofitting an existing portable oxygen concentrator for use in a patient ventilation system is contemplated, with the existing portable oxygen concentrator having at least one compressor, one or more sieve beds downstream of the compressor, one product tank downstream of the sieve beds, the product tank having an internal capacity of less than 300 ml (e.g. 50 to 100 ml for a typical portable oxygen concentrator), and a downstream gas path in fluid communication with the product tank, the downstream gas path having at least one existing pressure regulator, one existing flow valve, and perhaps one existing filter integrated therein. The method is contemplated as comprising the steps of: (1) replacing the existing product tank with one of increased capacity or supplementing the existing product tank with one or more supplemental product tanks, such that the aggregate internal capacity of any product tank(s) is large enough to accommodate a normal patient breath size (e.g. 300 ml or more or preferably 500 ml or more); (2) placing a ventilation gas path in fluid communication with the downstream gas path; and (3) configuring the downstream gas flow path such that substantially all of the gas flowing into the downstream gas path from any product tank(s) flows to the ventilation gas path without flowing through (therefore effectively bypassing) any pressure regulator(s), flow valve(s) and/or filter(s).

It is contemplated that the ventilation gas path may comprise a pressure sensor. It is additionally contemplated that the configuring step may be performed by removing any existing pressure regulator, flow valve and filter. It is further contemplated that the configuring step may be performed by placing the ventilation gas path in fluid communication with the downstream gas path upstream from any existing pressure regulator, flow valve and filter, and diverting substantially all of the gas flowing into the downstream gas path to the ventilation gas path.

It is further contemplated that the existing portable oxygen concentrator may comprise an existing external housing, and wherein following performance of the method, no portion of any existing or supplemental product tank is outside of the existing external housing.

BRIEF DESCRIPTION OF THE DRAWINGS

These and other features and advantages of the various embodiments disclosed herein are better understood with respect to the following descriptions and drawings, in which.

DETAILED DESCRIPTION

According to various aspects of the present disclosure, retrofitted portable oxygen concentrator systems and methods of manufacturing a retrofitted portable oxygen concentrator system from an existing portable oxygen concentrator are contemplated. The retrofit process involves (1) replacing and/or supplementing the preexisting product tank of the existing portable oxygen concentrator such that the overall internal volume of the product tank(s) within the retrofitted portable oxygen concentrator meets or exceeds a volume that can accommodate a normal patient breath size (e.g. 300 ml or more or preferably 500 ml or more); and (2) bypassing the preexisting pressure regulator and/or flow valve and/or filter such that substantially all of the gas output from the product tank(s) may be output to a ventilator or otherwise used in a patient ventilation system (e.g. used for integrated ventilator functionality of the retrofitted portable oxygen concentrator system) without encountering the preexisting pressure regulator and/or flow valve and/or filter. In such a way, it may be seen that oxygen-enriched gas may be output from the retrofitted portable oxygen concentrator system at pressures sufficient to enable direct interfacing with a portable, wearable ventilator without requiring further input of pressurized gas from an additional pressurized gas source. The oxygen-enriched gas output from the retrofitted portable oxygen concentrator may also be configured in various ways to increase the volume of gas delivered to the ventilator or ventilator functionality without requiring the presence of further pressurized gas sources, such as via various entrainment systems which may increase the volume while lowering the overall oxygen concentration of the gas delivered to the ventilator proportionally, which may permit a mode of combined ventilation/oxygen supplementation therapy whereby the patient receives a moderately oxygen-enriched ventilation gas with an oxygen concentration between the highly enriched oxygen gas output by the portable oxygen concentrator and the non-enriched atmospheric gas that would be output by a compressor alone.

Figure 1:
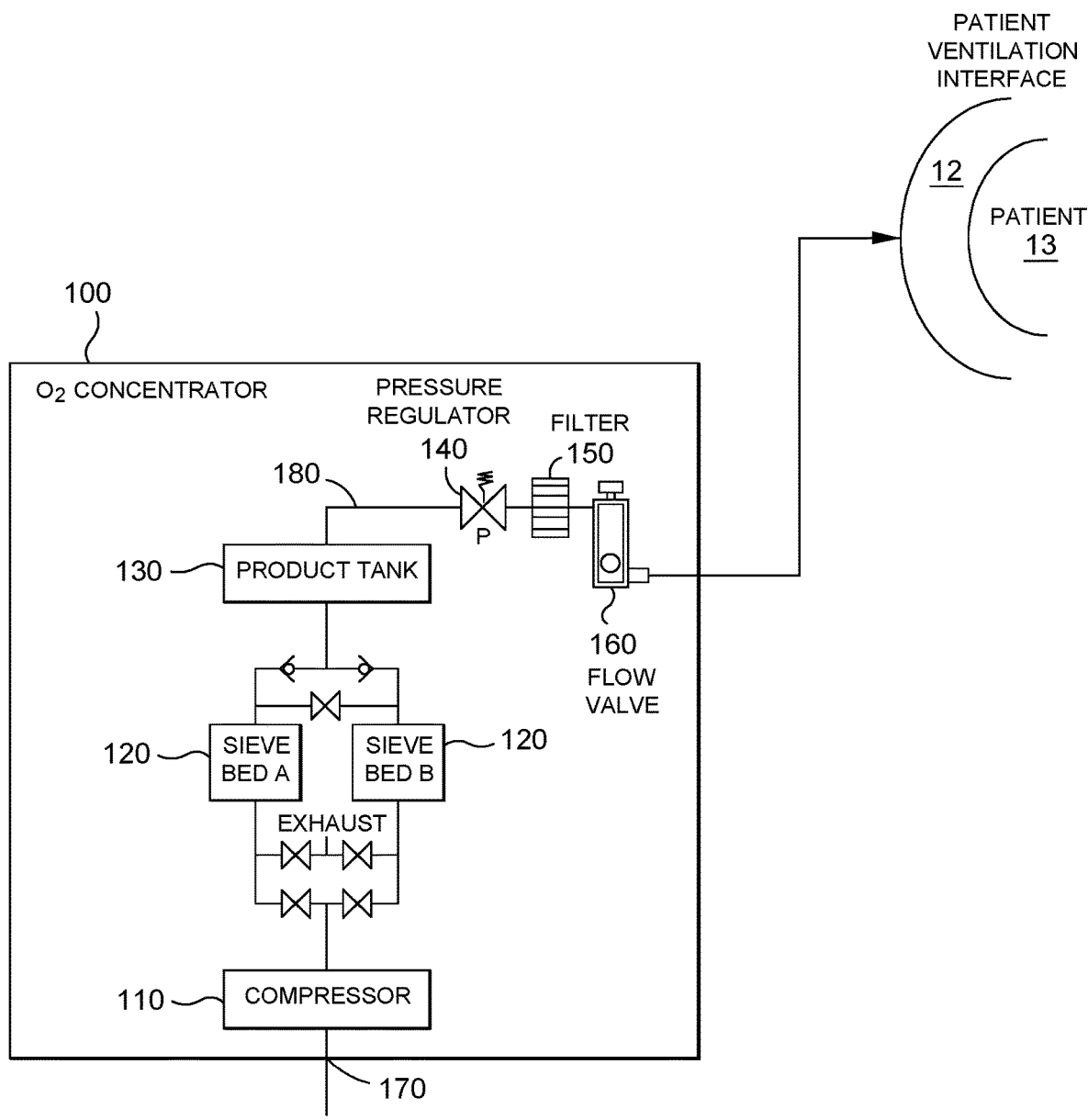
FIG. 1 is a schematic of a PSA portable oxygen concentrator prior to a retrofit according to one or more embodiments of the present disclosure.

Turning now to FIG. 1, a schematic of an exemplary portable oxygen concentrator 100 is shown prior to a retrofit as described herein. As may be seen, the exemplary existing portable oxygen concentrator 100 has a compressor 110, two sieve beds 120, a product tank 130, a pressure regulator 140, a filter 150, and a flow valve 160. Functionality of the depicted existing portable oxygen concentrator 100 is achieved through the well-known technique of Pressure Swing Adsorption (PSA). Specifically, the exemplary PSA portable oxygen concentrator 100 operates by the compressor 110 intaking ambient air through an intake 170 and compressing it to a high pressure, typically around 25 PSI. Through the coordination of various valves, the compressed ambient air is introduced into sieve bed A of the sieve beds 120. The material of sieve bed A, when pressurized to this pressure, preferentially adsorbs large quantities of nitrogen gas, permitting a highly oxygen-enriched gas to flow through the sieve bed 120 and into the product tank 130, typically achieving an oxygen concentration in the product tank 130 of around 93%. Once the first sieve bed 120 is approaching saturation with nitrogen, the valves will operate to redirect the flow of the compressor to sieve bed B of the sieve beds 120, which functions identically to sieve bed A to output highly enriched oxygen gas to the product tank 130. While the compressor 110 is flowing compressed ambient air to sieve bed B, sieve bed A is closed off from the product tank 130 and the compressor 110, and opened to the ambient air. The resulting pressure drop in sieve bed A causes the adsorbed nitrogen to desorb from the material of the sieve bed 120 (typically a zeolite) and exhaust to the atmosphere, regenerating the ability of the sieve bed A to adsorb further nitrogen. Once sieve bed B is approaching saturation, the output from the compressor 110 will be switched back to sieve bed A, permitting sieve bed B to be opened to ambient air and depressurized, causing it to exhaust its adsorbed nitrogen. Through repeating this cycle of pressure swings between the sieve beds 120, it may be seen that an essentially uninterrupted production of highly enriched oxygen gas may be achieved.

In such an exemplary portable oxygen concentrator 100, the output from the product tank 130 is flowed through a downstream gas flow path 180 where it may encounter one or more of a pressure regulator 140 or a flow valve 160, and also may encounter a filter 150, prior to being output from the portable oxygen concentrator 100. The function of the pressure regulator 140 may be to reduce the pressure of the oxygen-enriched gas contained in the product tank 130 without necessarily diluting the oxygen content of the oxygen-enriched gas. The function of the filter 150 may be to prevent passage of solid particulate matter to the patient 13 which may have been introduced into the concentrator 100 via the compressor intake 170, or other sources of solid particulate matter which may enter into the downstream gas path 180, such as broken-off particles of sieve bed material. The function of the flow valve 160 may be to alter the flow characteristics of the highly enriched gas output from the oxygen concentrator 100, such as increasing or reducing the volume flowed out via expansion or constriction of the size of a passageway, or, especially in smaller wearable/carriable embodiments of portable oxygen concentrators, via configuring the output of oxygen-enriched gas to occur in a pulsed mode whereby a bolus of a specified volume of gas is caused to emit from the flow valve 160 at specified intervals, with these volumes and/or intervals generally being adjustable by the patient 13 according to their oxygen needs. Once emitted, regardless of whether in a pulsed mode or in a continuous flow mode, the enriched oxygen gas is generally carried to the patient 13 through a patient apparatus 12, with the patient ultimately inspiring the enriched oxygen gas.

Figure 2:
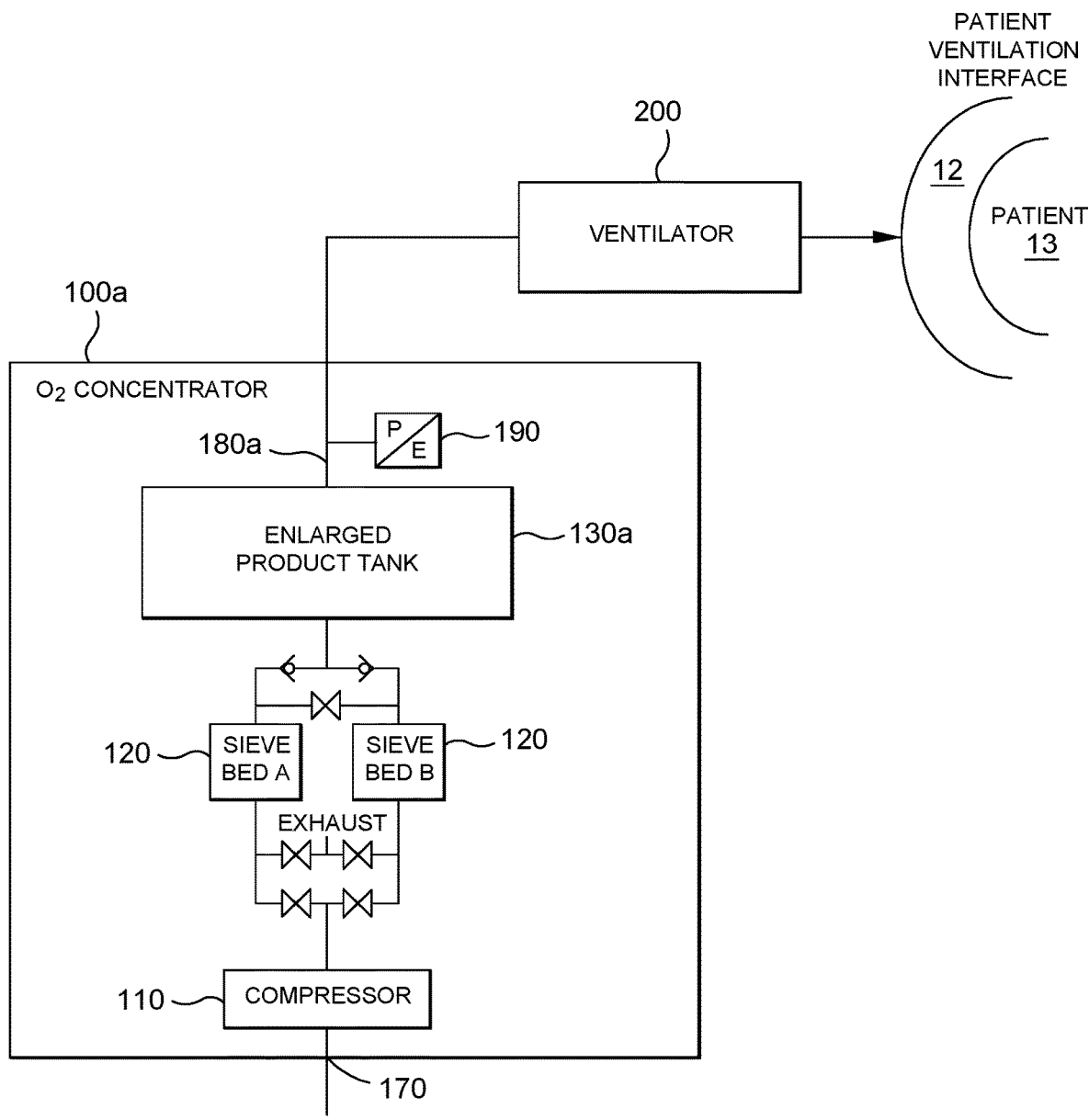
FIG. 2 is a schematic of a first embodiment of a retrofitted portable oxygen concentrator.

Turning now to FIG. 2, a first exemplary embodiment of a retrofitted portable oxygen concentrator 100a is shown. As may be seen, in this first exemplary embodiment, the existing product tank 130 has been removed and replaced with a single enlarged product tank 130a of comparatively greater volume than the original. In this particular embodiment, the single enlarged product tank 130a has a total internal capacity of 300 ml or greater. Further, the pressure regulator 140, filter 150, and flow valve 160 present in the downstream gas path 180 from the product tank 130 have been removed, and the downstream gas path from the enlarged product tank 130a now instead outputs to or otherwise has been replaced with a ventilation gas path 180a which contains a pressure sensor 190.

Figure 3:
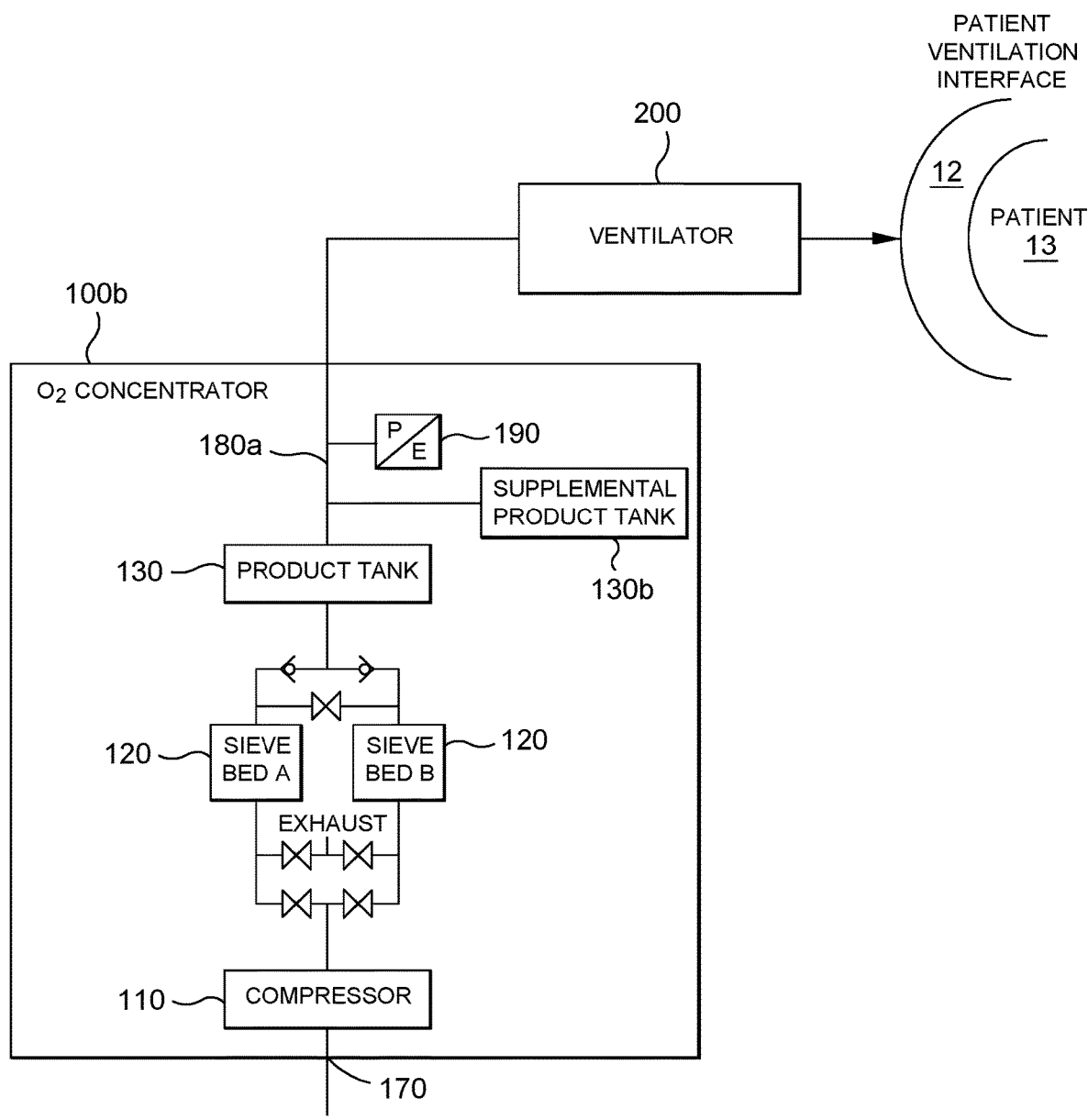
FIG. 3 is a schematic of a second embodiment of a retrofitted portable oxygen concentrator.

Turning now to FIG. 3, a second exemplary embodiment of a retrofitted portable oxygen concentrator 100b is shown. In this second exemplary embodiment, it may be seen that instead of replacing the existing product tank 130 with an enlarged product tank 130a, the existing product tank 130 has been maintained, with a supplemental product tank 130b also provided. In this embodiment, while the existing product tank 130 by itself may not have a total internal capacity of 300 ml or greater, the aggregate internal capacity of the existing product tank 130 and the supplemental product tank 130b together is large enough to accommodate a normal patient breath size (e.g. 300 ml or greater or more preferably 500 ml or greater).

As may be appreciated, the retrofitted portable oxygen concentrator 130a, 130b is not limited to the two exemplary embodiments, but rather the retrofit process may be accomplished in a number of fashions. For example, the existing product tank 130 may be replaced with one or more supplemental product tanks 130b or left in place or relocated while also being supplemented by one or more supplemental product tanks 130b. The important consideration is that the total aggregate internal capacity of the product tanks 130, 130a, 130b to which the enriched oxygen gas is output to from the sieve beds 120 be large enough to accommodate a normal patient breath size (e.g. 300 ml or greater or more preferably 500 ml or greater), and the retrofitted portable oxygen concentrator 100a, 100b is configured such that substantially all of the gas flowing from the ultimate configuration of the product tank(s) 130, 130a, 130b flows to the ventilation gas path 180a and substantially none of the gas flows to or through any of a pressure regulator 140, a flow valve 160, and/or a filter 150. It may be seen that in some embodiments, the product tank(s) 130, 130a, 130b of the retrofitted portable oxygen concentrator 100a, 100b may be entirely contained within the existing housing provided with the original portable oxygen concentrator 100, which may be accomplished, for example, via the removal of certain portions not necessary in the final retrofitted portable oxygen concentrator 100a, 100b such as pressure regulators 140, filters 150, and flow valves 160. It may also be seen that in other embodiments, the supplemental product tank 130b which may or may not be a replacement for existing product tank 130, may be provided as an attachment to the existing portable oxygen concentrator housing or otherwise at least partially protrude outside of the existing housing.

With regard to the ventilation gas path 180a, the important consideration is that the ventilation gas path 180a be configured such that substantially all of the gas flowing from the enlarged product tank 130a or the existing product tank 130 with one or more supplemental product tanks 130b flows to the ventilation gas path 180a without flowing through any pressure regulators 140, flow valve 160 or filter 150. This may be achieved in a number of ways. In the exemplary embodiments, the pressure regulator 140, flow valve 160 and/or filter 150 may be removed entirely. In other embodiments, however, it may be seen that any one or more of these same components may instead be bypassed, for example, such that the ventilation gas path 180a may be fluidly connected to the downstream gas path 180 upstream of any pressure regulator 140, flow valve 160 and/or filter 150, with the downstream gas path 180 blocked off downstream of the point where the ventilation gas path 180a connects to it and upstream of any pressure regulator 140, flow valve 160 and/or filter 150.

It is further contemplated that a pressure sensor 190 may be arranged to measure the pressure in the product tank 130, 130a, 130b. For example, the ventilation gas path 180a may include a pressure sensor 190, or a pressure sensor 190 may be upstream of the product tank 130, 130a, 130b. The pressure sensor 190 may be operative to sense the pressure of the gas in the product tank 130, 130a, 130b or flowing through the ventilation gas path 180a, and may sense pressure directly, such as through force collection (i.e. diaphragms, pistons, bourdon tubes, or bellows) or through piezoresistive, piezoelectric, capacitive, electromagnetic, potentiometric, or optical methods, or may measure pressure through other means, such as through resonant, thermal or ionization means. The pressure sensor 190 may also be another type of sensor which may be used, alone or in combination with other components, to derive the pressure of the gas flowing through the ventilation gas path 180*a* via measuring something other than pressure. For example, but without limitation, the pressure sensor 190 may be another type of sensor such as a flow meter which, alone or in coordination with other sensors or components either within the retrofitted portable oxygen concentrator 100*a*, 100*b* or external thereto (such as within a portable ventilator 200 with which the sensor may communicate), may function to derive the pressure as a function of measured flow.

The above description is given by way of example, and not limitation. Given the above disclosure, one skilled in the art could devise variations that are within the scope and spirit of the invention disclosed herein. Further, the various features of the embodiments disclosed herein can be used alone, or in varying combinations with each other and are not intended to be limited to the specific combination described herein. Thus, the scope of the claims is not to be limited by the exemplary embodiments.

What is claimed is:

1. A method of retrofitting an existing portable oxygen concentrator for use in a patient ventilation system, the existing portable oxygen concentrator having at least one compressor, one or more sieve beds downstream of the compressor, an existing product tank downstream of the sieve beds, the existing product tank having an internal capacity of less than 300 ml, and a downstream gas path in fluid communication with the existing product tank, the downstream gas path having at least one pressure regulator integrated therein, the method comprising:

replacing or supplementing the existing product tank to define a retrofit set of one or more product tanks, the retrofit set of one or more product tanks including either i) the existing product tank and one or more supplemental product tanks or ii) one or more replacement product tanks, the aggregate internal capacity of the retrofit set of one or more product tanks being 300 ml or more; and placing a ventilation gas path in fluid communication with the downstream gas path at a location upstream from the at least one pressure regulator such that gas flowing from the retrofit set of one or more product tanks flows to the ventilation gas path without flowing through the at least one pressure regulator.

2. The method of claim 1, wherein said configuring includes removing the at least one pressure regulator.

3. The method of claim 1, wherein the downstream gas path has at least one filter integrated therein.

4. The method of claim 3, wherein the location is upstream from the at least one filter such that the gas flowing from the retrofit set of one or more product tanks flows to the ventilation gas path without flowing through the at least one filter.

5. The method of claim 3, wherein said configuring includes removing the at least one filter.

6. The method of claim 1, wherein the downstream gas path has at least one flow valve integrated therein.

7. The method of claim 6, wherein the location is upstream from the at least one flow valve such that the gas flowing from the retrofit set of one or more product tanks flows to the ventilation gas path without flowing through the at least one flow valve.

8. A method of retrofitting an existing portable oxygen concentrator for use in a patient ventilation system, the existing portable oxygen concentrator having at least one compressor, one or more sieve beds downstream of the compressor, an existing product tank downstream of the sieve beds, the existing product tank having an internal capacity of less than 300 ml, and a downstream gas path in fluid communication with the existing product tank, the downstream gas path having at least one pressure regulator integrated therein, the method comprising:

replacing or supplementing the existing product tank to define a retrofit set of one or more product tanks, the retrofit set of one or more product tanks including either i) the existing product tank and one or more supplemental product tanks or ii) one or more replacement product tanks, the aggregate internal capacity of the retrofit set of one or more product tanks being 300 ml or more;

placing a ventilation gas path in fluid communication with the retrofit set of one or more product tanks; and configuring the portable oxygen concentrator such that all of the gas flowing from the retrofit set of one or more product tanks flows to the ventilation gas path and none flows through the at least one pressure regulator, wherein the downstream gas path has at least one flow valve integrated therein and the portable oxygen concentrator is configured such that none of the gas flowing from the retrofit set of one or more product tanks flows through the at least one flow valve.

9. The method of claim 8, wherein said configuring includes placing the ventilation gas path in fluid communication with the downstream gas path at a location upstream from the at least one pressure regulator and the at least one flow valve and diverting all of the gas flowing into the downstream gas path to the ventilation gas path.

10. The method of claim 8, wherein said configuring includes removing the at least one flow valve.

11. The method of claim 10, wherein said configuring includes removing the at least one pressure regulator.

12. The method of claim 1, wherein the ventilation gas path comprises a pressure sensor.

13. The method of claim 1, wherein the existing portable oxygen concentrator comprises an existing external housing, and wherein following performance of the method, no portion of the retrofit set of one or more product tanks is outside of the existing external housing.

14. The method of claim 1, wherein the aggregate internal capacity of the retrofit set of one or more product tanks is 500 ml or more.

15. A method of retrofitting an existing portable oxygen concentrator for use in a patient ventilation system, the existing portable oxygen concentrator having at least one compressor, one or more sieve beds downstream of the compressor, an existing product tank downstream of the sieve beds, the existing product tank having an internal capacity of less than 300 ml, and a downstream gas path in fluid communication with the existing product tank, the downstream gas path having at least one pressure regulator integrated therein, the method comprising:

replacing the existing product tank with one or more replacement product tanks, the aggregate internal capacity of the one or more replacement product tanks being 300 ml or more; and placing a ventilation gas path in fluid communication with the downstream gas path at a location upstream from the at least one pressure regulator such that gas flowing from the one or more replacement product tanks flows to the ventilation gas path without flowing through the at least one pressure regulator.

16. The method of claim 15, wherein the one or more replacement product tanks includes an enlarged product tank having an internal capacity of 300 ml or more.

17. The method of claim 15, wherein the aggregate internal capacity of the one or more replacement product tanks is 500 ml or more.

18. A method of retrofitting an existing portable oxygen concentrator for use in a patient ventilation system, the existing portable oxygen concentrator having at least one compressor, one or more sieve beds downstream of the compressor, an existing product tank downstream of the sieve beds, the existing product tank having an internal capacity of less than 300 ml, and a downstream gas path in fluid communication with the existing product tank, the downstream gas path having at least one pressure regulator integrated therein, the method comprising:

supplementing the existing product tank with one or more supplemental product tanks, the aggregate internal capacity of the existing product tank and the one or more supplemental product tanks being 300 ml or more; and placing a ventilation gas path in fluid communication with the downstream gas path at a location upstream from the at least one pressure regulator such that gas flowing from the existing product tank and the one or more supplemental product tanks flows to the ventilation gas path without flowing through the at least one pressure regulator.

19. The method of claim 18, wherein the aggregate internal capacity of the existing product tank and the one or more supplemental product tanks is 500 ml or more.

* * * * *